United States Patent
Jones et al.

(10) Patent No.: US 10,012,761 B2
(45) Date of Patent: Jul. 3, 2018

(54) RECONSTRUCTING DEAD OIL

(75) Inventors: Christopher M. Jones, Houston, TX (US); Michael T. Pelletier, Houston, TX (US); Abbas Sami Eyuboglu, The Woodlands, TX (US); Cyrus Aspi Irani, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 13/878,588

(22) PCT Filed: Oct. 27, 2010

(86) PCT No.: PCT/US2010/054200
§ 371 (c)(1),
(2), (4) Date: Apr. 10, 2013

(87) PCT Pub. No.: WO2012/057740
PCT Pub. Date: May 3, 2012

(65) Prior Publication Data
US 2013/0197809 A1    Aug. 1, 2013

(51) Int. Cl.
*E21B 49/08* (2006.01)
*E21B 49/10* (2006.01)
*G01N 33/24* (2006.01)
*G01V 9/00* (2006.01)
*G01V 99/00* (2009.01)
*G01N 1/00* (2006.01)

(52) U.S. Cl.
CPC ............... *G01V 9/00* (2013.01); *G01N 1/00* (2013.01); *G01V 99/00* (2013.01); *E21B 49/08* (2013.01); *E21B 49/10* (2013.01); *E21B 2049/085* (2013.01); *G01N 33/241* (2013.01)

(58) Field of Classification Search
CPC .......... G01V 9/00; G01V 9/007; G01V 11/00; G01N 24/081; E21B 49/08
USPC .......................................................... 702/11
See application file for complete search history.

(56) References Cited

U.S. PATENT DOCUMENTS

| | | |
|---|---|---|
| 5,934,374 A | 8/1999 | Hrametz et al. |
| 6,737,864 B2 | 5/2004 | Prammer et al. |
| 6,888,127 B2 | 5/2005 | Jones et al. |
| 6,912,898 B2 | 7/2005 | Jones et al. |
| 6,950,750 B1 | 9/2005 | Carpentier |
| 6,967,322 B2 | 11/2005 | Jones et al. |

(Continued)

OTHER PUBLICATIONS

Pedersen et al., Phase Behavior of Petroleum Reservoir Fluids, 2007 by Taylor & Francis Group, LLC CRC Press is an imprint of Taylor & Francis Group, an Informa business.*

(Continued)

*Primary Examiner* — Michael Dalbo
(74) *Attorney, Agent, or Firm* — Howard L. Speight, PLLC

(57) ABSTRACT

A computer accepts dead-oil properties of a reservoir fluid sampled from a well. The dead-oil properties are the measured composition of the reservoir fluid after volatile components of the reservoir have substantially vaporized. The computer analyzes the dead-oil properties and a constraint to produce estimated live-oil properties of the reservoir fluid. The live-oil properties are the composition of the reservoir before the volatile components have substantially vaporized. The computer uses the estimated live-oil properties to make a decision regarding the well.

11 Claims, 9 Drawing Sheets

(56) References Cited

U.S. PATENT DOCUMENTS

| | | | |
|---|---|---|---|
| 7,195,731 B2 | 3/2007 | Jones | |
| 7,337,660 B2 | 3/2008 | Ibrahim et al. | |
| 7,372,264 B2 | 5/2008 | Akkurt et al. | |
| 7,490,664 B2 | 2/2009 | Skinner et al. | |
| 7,516,788 B2 | 4/2009 | Gleitman et al. | |
| 7,571,644 B2 | 8/2009 | Ibrahim et al. | |
| 2003/0062472 A1 | 4/2003 | Mullins et al. | |
| 2004/0164237 A1 | 8/2004 | Jones et al. | |
| 2005/0005694 A1 | 1/2005 | Jones et al. | |
| 2005/0012244 A1 | 1/2005 | Jones | |
| 2005/0242807 A1 | 11/2005 | Freedman | |
| 2006/0155474 A1* | 7/2006 | Venkataramanan et al. | 702/13 |
| 2006/0241866 A1* | 10/2006 | DiFoggio | 702/12 |
| 2006/0250130 A1 | 11/2006 | Akkurt et al. | |
| 2007/0178011 A1 | 8/2007 | Elrod et al. | |
| 2007/0259433 A1 | 11/2007 | Jones et al. | |
| 2008/0087470 A1* | 4/2008 | Villareal | E21B 17/16 175/50 |
| 2008/0097735 A1 | 4/2008 | Ibrahim et al. | |
| 2008/0099241 A1 | 5/2008 | Ibrahim et al. | |
| 2008/0141767 A1* | 6/2008 | Raghuraman et al. | 73/152.55 |
| 2008/0202747 A1 | 8/2008 | Gleitman et al. | |
| 2008/0216559 A1 | 9/2008 | Hilab | |
| 2009/0032249 A1* | 2/2009 | Morales et al. | 166/250.01 |
| 2009/0192768 A1 | 7/2009 | Zuo et al. | |
| 2009/0248310 A1* | 10/2009 | Zuo et al. | 702/11 |
| 2010/0065268 A1* | 3/2010 | Gates et al. | 166/268 |
| 2010/0089132 A1 | 4/2010 | Larter et al. | |
| 2010/0229623 A1* | 9/2010 | Abad | E21B 49/08 73/1.02 |
| 2010/0252258 A1* | 10/2010 | Pelletier | E21B 49/10 166/264 |
| 2010/0271019 A1* | 10/2010 | Anand et al. | 324/303 |
| 2011/0048700 A1 | 3/2011 | Van Zuilekom et al. | |
| 2011/0088949 A1* | 4/2011 | Zuo et al. | 175/48 |

OTHER PUBLICATIONS

Manshad et al., Application of Continuous Polydisperse Molecular Thermodynamics for Modeling Asphaltene Precipitation in Crude Oil Systems, Energy & Fuels 2008, 22, 2678-2686.*

Instituto Mexicano De La Propiedad Industrial, Communication of Results from Examination, File MX/a/2013/004483, which is the counterpart MX patent application to the instant application, dated Mar. 13, 2014.

Instituto Mexicano De La Propiedad Industrial, Translation of Communication of Results from Examination, File MX/a/2013/004483, which is the counterpart MX patent application to the instant application, dated Mar. 13, 2014.

IP Australia, Discovery House, Phillip Act 2606, Australia, Patent Examination Report No. 1, Australian Patent Application No. 2010363053 (which is the Australian counterpart of the instant application), dated Jul. 26, 2013

Instituto Mexicano De La Propiedad Industrial, Communication of Results from Examination (3rd Office Action), File MX/a/2013/004483, which is the counterpart MX patent application to the instant application, dated Oct. 15, 2014.

Instituto Mexicano De La Propiedad Industrial, Translation of Communication of Results from Examination, (2nd Office Action), File MX/a/2013/004483, which is the counterpart MX patent application to the instant application, dated Oct. 15, 2014.

Patent Office of the Cooperation Council for the Arab States of the Gulf, Search Report, Application No. GC 2011-19638, which is a counterpart of the instant application, dated Nov. 11, 2014.

Instituto Mexicano De La Propiedad Industrial, Communication of Results from Examination (2nd Office Action), File MX/a/2013/004483, which is the counterpart MX patent application to the instant application, dated Jul. 16, 2014.

Instituto Mexicano De La Propiedad Industrial, Translation of Communication of Results from Examination (2nd Office Action), File MX/a/2013/004483, which is the counterpart MX patent application to the instant application, dated Jul. 16, 2014.

GCC Patent Office, Patent Office of the Cooperation Council for the Arab States of the Gulf, Application No. GC 2011-19638, which is a GCC counterpart to the instant application, May 18, 2015.

IP Australia, Discovery House, Phillip Act 2606, Australia, Notice of Acceptance, Australian Patent Application No. 201036053 (which is the Australian counterpart of the instant application), dated May 4, 2015.

Instituto Mexicano De La Propiedad Industrial, Communication of Results from Examination (4th Office Action), File MX/a/2015/000618, which is the counterpart MX patent application to the instant application, dated Jan. 22, 2015.

Translation of Instituto Mexicano De La Propiedad Industrial, Communication of Results from Examination (4th Office Action), File MX/a/2015/000618, which is the counterpart MX patent application to the instant application, dated Jan. 22, 2015.

Instituto Mexicano De La Propiedad Industrial, Notice of Allowance, Application No. MX/2015/038039, which is an MX counterpart of the instant application, dated Jun. 10, 2015.

Australian Government IP Australia, Patent Examination Report No. 1, Patent Application No. 2015213292, which is an AU counterpart to the instant application, dated Apr. 5, 2016.

Patent Office of the Cooperation Council for the Arab States of the Gulf, GCC Patent Office, Examination Report, Application No. GC 2011-29895, which is a GCC counterpart to the instant application, dated May 29, 2016.

* cited by examiner

RECONSTRUCTING DEAD OIL

BACKGROUND

Exploration wells are often drilled for the purpose of discovering petroleum reserves. Determining such reserves may include, among other things, determining oil bearing zones, petroleum in place, recoverable petroleum, and value of petroleum. Determining recoverable petroleum and the value of petroleum often involves collecting a sample of fluid at reservoir conditions. For the purpose of this application, this sample is called a "live fluid" or "live oil."

A composition (or assay) of the fluid may be used to determine the value of the fluid, but also physical properties of the fluid such as Gas to Oil Ratio ("GOR"), bubble point, viscosity, wax precipitation point, asphaltene precipitation point, and purely chemical properties such as compatibility with other fluid, scaling issues, hydrate formation properties, etc. The ability of analysis to determine the properties listed above and others may hinge on the drilling fluid filtrate contamination level of the fluids especially when the drilling contaminate is organic based mud (drilling fluid) filtrate ("OBM" filtrate).

In practice many properties of a contaminated sample may be backed out if the contamination level is known. In some circumstances, other properties of the drilling fluid may not be backed out and may be determined only with sufficiently pristine samples. Some properties of the fluid are well defined by equation-of-state models that often are functions solely of live fluid composition. Therefore, it is useful to determine live fluid composition from a live fluid sample. Determining live fluid composition can be challenging, especially in a down hole environment.

BRIEF DESCRIPTION OF THE DRAWINGS

In FIGS. 8-12, the horizontal axis is wavelength in nanometers and the vertical axis is optical density.

FIG. 9 is the optical density of a dead oil sample measured in the same experiment.

FIG. 10 is a graph of the optical density of the dead oil sample shown in FIG. 9 recombined with flashed gases.

FIG. 11 is a graph of the optical density of the recombined dead oil that substantially matches the optical density of the live oil shown in FIG. 8.

FIG. 12 shows FIGS. 8-11 overlaid on each other.

DETAILED DESCRIPTION

Figure 1:
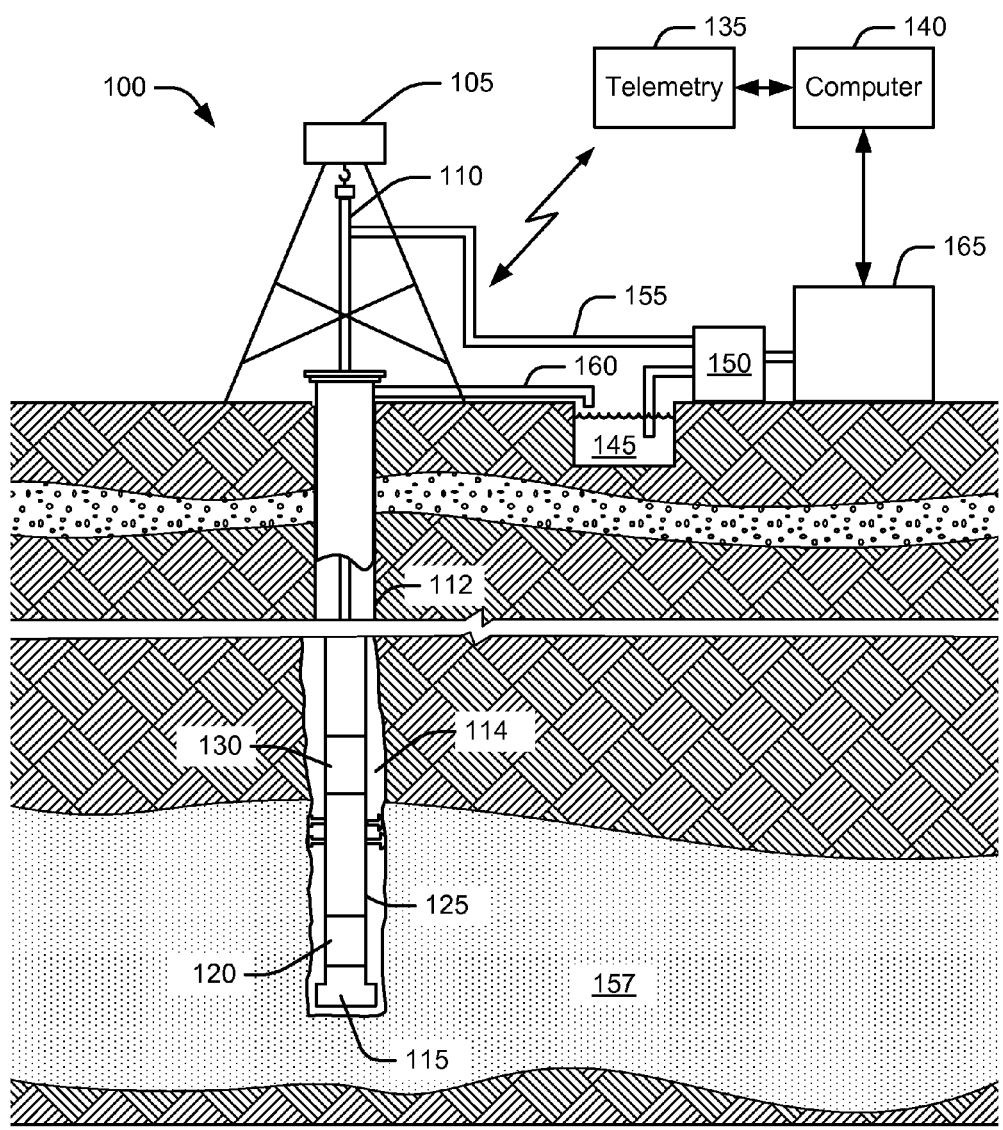
FIG. 1 is an illustration of an oil field environment.

In one embodiment, an example environment 100, illustrated in FIG. 1, includes a derrick 105 from which a drill string 110 is suspended in a borehole 112. FIG. 1 is greatly simplified and for clarity does not show many of the elements that are used in the drilling process. In one embodiment, the volume within the borehole 112 around the drill string 110 is called the annulus 114. In one embodiment, the drill string includes a bit 115, a variety of actuators and sensors, shown schematically by element 120, a formation testing tool 125, and a telemetry section 130, through which the downhole equipment communicates with a surface telemetry system 135. In one embodiment, a computer 140, which in one embodiment includes input/output devices, memory, storage, and network communication equipment, including equipment necessary to connect to the Internet, receives data from the downhole equipment and sends commands to the downhole equipment.

In one embodiment, the example environment 100 includes a drilling mud circulation system. Drilling mud is used to cool the bit, carry cuttings to the surface, and keep the bore hole from collapsing. In one embodiment, drilling mud is self-containing. That is, its properties keep it from seeping into the formation surrounding the borehole. In one embodiment, drilling mud begins its circulation in a mud pit 145. In one embodiment, the mud is pumped out of the mud pit 145 by a mud pump 150 through a pipe 155 to the drill string 110. In one embodiment, the mud travels down the drill string 110 and exits through the bit 115. It one embodiment, the mud, carrying cuttings from the formation 157, flows through the annulus 114 to the surface where it is returned to the mud pit 145 by a pipe 160.

One embodiment of the example embodiment 100 includes an analysis system 165, which analyzes cuttings and mud that is either manually or automatically extracted from the mud pit through, for example, the mud pump 150. In one embodiment, the results produced by the analysis system 165 are provided to the computer 140.

The equipment and techniques described herein are also useful in a wireline or slickline environment. In one embodiment, for example, a formation testing tool may be lowered into the borehole 112 using wired drillpipe, wireline, coiled tubing (wired or unwired), or slickline. In one embodiment of a measurement-while-drilling or logging-while-drilling environment, such as that shown in FIG. 1, power for the formation testing tool is provided by a battery, by a mud turbine, or through a wired pipe from the surface, or through some other conventional means. In one embodiment of a wireline or slickline environment, power is provided by a battery or by power provided from the surface through the wired drillpipe, wireline, coiled tubing, or slickline, or through some other conventional means.

In one embodiment, the composition of live fluid can be estimated from oil that has lost volatile components (or "dead oil") if certain assumptions are made. In one embodiment, compositional equations of state can be applied to such a live-oil-estimated composition to estimate many of the physical properties of oil. In one embodiment, recombination of the dead oil to a pseudo live oil composition allows many of the physical properties of the reservoir live oil to be estimated. In one embodiment, the estimated live oil composition allows a better estimate of drilling fluid filtrate contamination to be made than that beginning with dead oil.

A compositional assay can be performed with small quantities of fluid. For example, gas chromatography, optical spectroscopy, isotope ratio mass spectroscopy, quadropole mass spectroscopy, Fourier transform ion cyclotron resonance, liquid chromatography, pyrolysis techniques, thermal extraction techniques and others require only micro liters for analysis. Many of these techniques are already performed at a well site usually in a surface data logging unit, which in one embodiment are included in the analysis system 165 shown in FIG. 1.

Figure 2:
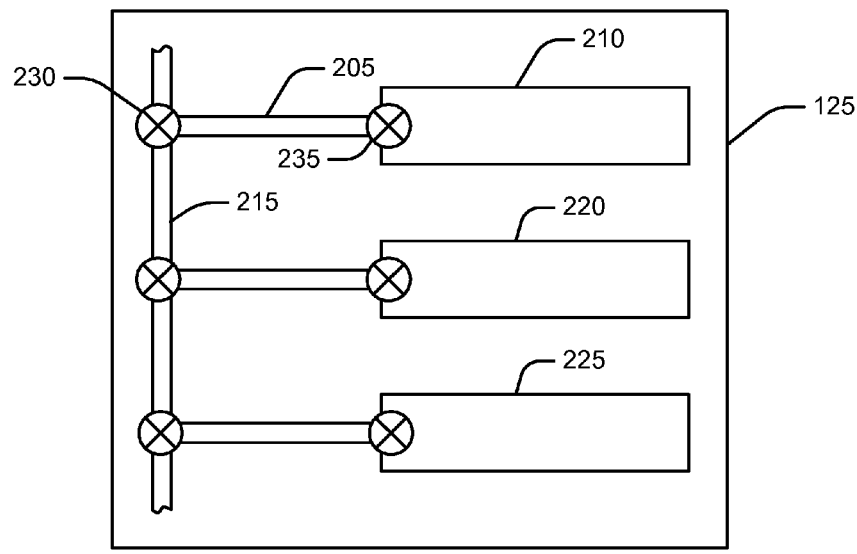
FIG. 2 is an illustration of a portion of a formation testing tool.

One embodiment of the formation testing tool 125, illustrated in FIG. 2, includes a manifold 215 for carrying sampled reservoir fluid (i.e., fluid sampled from the reservoir) to one or more sample chambers 210, 220, 225, etc. (while three sample chambers are shown in FIG. 2, it will be understood that the formation testing tool can contain a smaller or larger number of sample chambers). The formation testing tool 125 includes a tube 205 for carrying sampled reservoir fluid from the manifold 215 to sample chamber 210. In one embodiment, during sampling, a small (on the order of a milliliter) quantity of petroleum is trapped in the tube 205. A first valve 230 couples the tube 205 to the manifold 215 and a second valve 235 couples the tube to the sample chamber 210. The first valve 230 and the second valve 235 are closeable so that the tube 205 can be removed from between the manifold 215 and the sample chamber 210 while retaining the contents of the tube 205. Alternatively, the sample chamber 210 can be removed from the formation testing tool 125 and the contents of the tube 205 can remain undisturbed. In that way, the tube 205 will retain a sample that is relatively close to the live oil in terms of composition. Similar valving on the tubes leading to other sample chambers, e.g., 220 and 225, in the formation testing tool 125 allow additional small samples to be taken.

In one embodiment, the sample chambers 210, 220, and 225 are removable from the formation testing tool 125. In one embodiment, the tube 205 remains in the formation testing tool 125 after the sample chamber 210 is removed and can be removed later. In one embodiment, the tube 205 is not removed but the sample is extracted from the tube 205 while it remains in place in the formation testing tool 125.

In one embodiment, the sample remaining in the tube 205 is representative of the live oil trapped in the sampling container 210. In one embodiment, when the pressure inside the tube 205 reduces, e.g., because the sample chamber 201 is removed, the tube is removed from the formation testing tool 125, and/or the sample is removed from the tube 205, volatile components of the petroleum trapped within the tube 205 vaporize with reduced pressure leaving the sample trapped in the flow line 205 having the composition of a dead oil. That is, the dead oil trapped in the flow line 205 will have a composition similar to that of the live oil that was originally routed to the container but without the components that vaporized. The rate of vaporization is quick for some components such as methane, moderate for some components such as propane, and slow for other components such as butane and heavier components. The rate of flashing is related to the stability and concentration of that gas in the particular petroleum matrix sampled and the differential pressures and temperatures from reservoir conditions to well site conditions. The flashing process is governed by well defined principals such as Henry's Law, and is well defined by many equation-of-state models.

In one embodiment, rather than taking the samples down hole as described in the discussion of FIG. 2, dead oil samples are obtained from down hole cores or down hole cuttings. For example, in one embodiment, cuttings are extracted from the mud in the analysis system 165. In one embodiment, methods of extracting the fluids include centrifuging the sample, reflux extractions, or high pressure fluid extractions. Much of the surface contamination of drilling or coring fluids may be removed from the sample prior to extraction, however, these sample extracts are innately more contaminated with respect to properly sampled live oil fluids. One advantage of these methods is that baseline fluid contamination levels may be consistently monitored (in the case of drilling fluid composition logs for cuttings, or coring fluid baselines for cores) which improves the contamination assessment and mathematical removal of the contribution of the contaminants from compositional assays. In addition, gas show logs are often collected by surface data logging units which include composition of gas evolved from cuttings from depth, and volume of gas evolved from cuttings at depth and isotopes of gases evolved from cuttings at depth.

In one embodiment, quality control ("QC") information is collected on the live oil sample, and some down hole properties are collected on the live oil including oil density, viscosity, resistivity, capacitance, optical information, compressibility, GOR, NMR, etc. In one embodiment, little analysis is performed on a subset of the sample within the sample container due to the market preference to have full analysis performed in an advanced scientific laboratory setting. However, in one embodiment, it is useful to obtain as much information on the down hole sample as is possible without removing the sample from the container as early as possible after sampling (i.e., at the well site) even if the information is not as high quality as a scientific laboratory setting. In one embodiment, such on site testing would improve the turnaround time of such an analysis (i.e., up to 2 years in some cases with laboratories single supplier laboratories). Often, it is necessary to make multi-million dollar drilling decisions immediately during the drilling process for which immediate live oil fluid information is useful. It may take 3 months to obtain live oil fluid information from a scientific laboratory. Therefore, in one embodiment, it is useful to supply a live oil composition estimate from a dead oil and live oil properties as well as all derived information equation-of-state models provide therein.

Figure 3:
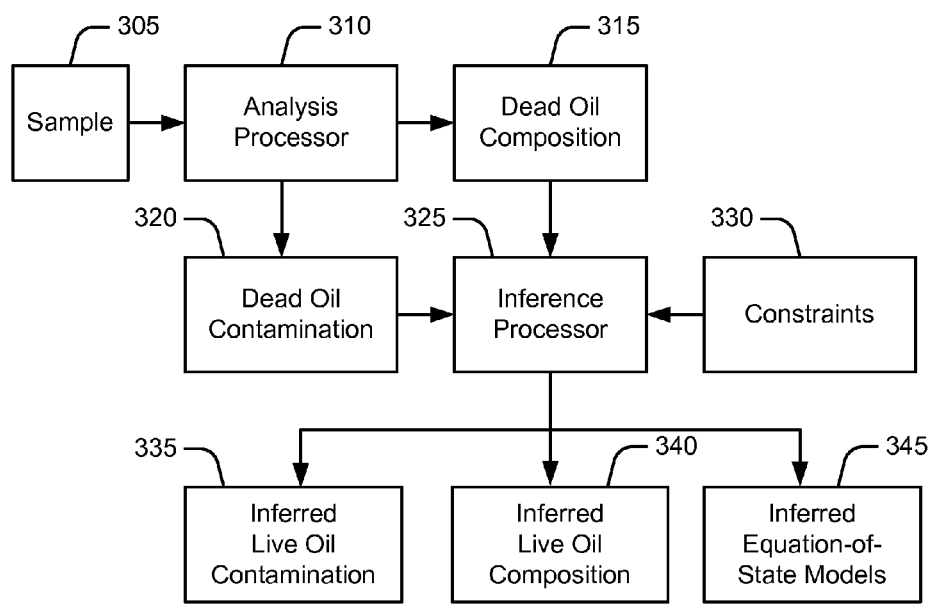
FIG. 3 is a block diagram of a system to infer a live oil composition, a live oil contamination and equation-of-state models from a dead oil sample.
Figure 10:
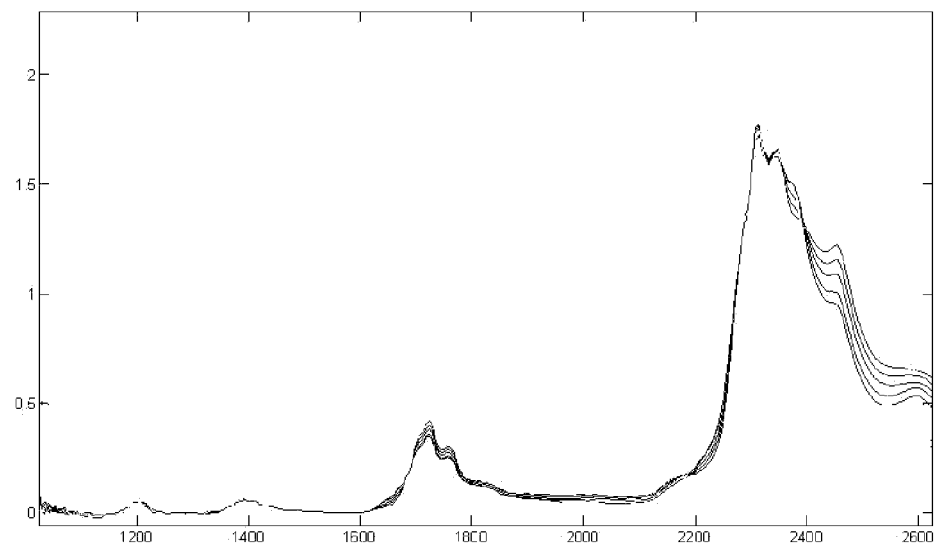

In one embodiment, a dead oil sample is analyzed as shown in FIG. 3. In one embodiment, the sample 305 is introduced to an analysis processor 310, i.e. one or more of the analytical instruments described herein coupled to one or more computers through the computers' input/output peripherals. In one embodiment, the analysis processor 310 generates a dead oil composition 315 and a dead oil contamination 320 of the sample 305 using the analytical instruments and known techniques for estimating the composition of, and contamination in, an oil sample. In one embodiment, the analysis processor uses the QC information and other properties that have been collected about the live oil. In one embodiment, an inference processor 325 uses the dead oil composition 315, the dead oil contamination 320, and a set of one or more constraints 330 to infer one or more of an inferred live oil contamination 335, an inferred live oil composition 340, and inferred equation-of-state models 345 for the live oil. In one embodiment, the analysis processor 310 and the inference processor 325 are parts of the analysis system 165. In one embodiment, the analysis processor 310 and the inference processor 325 are part of the computer 140. In one embodiment, the analysis processor 310 and the inference processor 325 are shared between the analysis system 165 and the computer 140. In one embodiment, the analysis processor 310 and the inference processor 325 are shared among the analysis system 165, the computer 140, and other computer resources disclosed herein, including down hole computer resources and computer resources that are remote from the environment 100 illustrated in FIG. 1 (e.g., see FIG. 10, discussed below).

The process of flashing defines how gas evolves from the petroleum matrix, but does not constrain the starting composition. In other words, the equations of state that mimic the thermodynamic process of flashing can predict the evolution from live oil to dead oil, but they may be unsolvable as, for example, a system of simultaneous equations with too many unknowns. In one embodiment, the constraints 330 provide the information from which inferences can be made so that the number of unknowns in the system of equations of state is reduced, which allows the system of equations to be solved. In one embodiment, the solution is the inferred live oil contamination 335 and the inferred live oil composition 340. The inferred equation-of-state models 345 reflect the inferences made to reduce the number of unknowns in the system of equations.

In one embodiment, the constraints 330 include at least one live oil property 330. In one embodiment, this property may be live oil density, live oil GOR, live oil compressibility, live oil viscosity, etc. In one embodiment, the constraints 330 include the composition of flashed gas and/or the volume of flashed gas.

In one embodiment, the inference processor 325 operates, in part, by mathematically adding a well-site-obtained gas chromatogram, which is a component-by-component composition as a function of boiling vapor pressure or boiling point, and the distribution of volatized gases the properties of the dead oil are simulated and volatile components into the mixture keeping the distribution fixed according to the flashing model as defined by principals such as Henry's Law, until simulations best match down hole measured or inferred properties such as density, bubble point, GOR, viscosity, compressibility etc. In one embodiment, additional constraints 330 for the equation-of-state modeling include the temperature and the pressure of the reservoir.

In one embodiment, a live oil composition 340 is directly inferred from a sample's dead oil composition 315 if the oil conforms to well defined patterns such as "normal marine", "log normal", or is well constrained by the basin, field, or source rock conditions. Isotopic fractionation is purely a mass kinetic effect constrained by temperature, whereas component fractionation is a chemical effect. In one embodiment, isotopic constraints included in constraints 330 are used by the inference processor 325 to reconstitute a known gas composition into a dead oil composition 315 to derive the live oil composition 340. In one embodiment, the process is similar to the isotopic distribution of carbon reservoirs on earth (e.g., forests, the ocean, carbonate formations etc.) for CO2.

In one embodiment, the constraints 330 include isotopic values or total GOR extracted from cuttings at the well site as well as the gas log composition that are used to mathematically estimate a live oil composition 340. In principal, cuttings contain mostly surface contamination of drilling fluid. In one embodiment, the cuttings are washed off with a compositionally identifiable fluid of different phase from the petroleum in the cuttings to remove much of the potential contamination. In one embodiment, the constraints 330 include the composition of the fluid used to wash the cuttings.

In one embodiment, the cuttings are pressure extracted using a chemically identifiable solvent and the quantitative dead oil composition 315 is determined by the analysis processor 310 using one of the compositional assay techniques described above, e.g. GC-MS or GC-FID.

In one embodiment, the constraints 330 include logs made of the drilling fluid filtrate. In one embodiment, the inference processor mathematically removes the drilling fluid filtrate contamination by subtracting the orthogonal components of contamination from the drilling fluid, which is the same process used to determine drilling fluid contamination in scientific laboratories.

In one embodiment, the constraints 330 include the volume of extract from the cuttings, the volume of rock removed by the drilling process, and the volumetric gas show information as a function of depth. In one embodiment, such constraints are used to determine the GOR and GOR composition. In one embodiment, this information and/or isotope information are used to derive the estimated live oil composition 340.

In one embodiment, surface data including the derived live oil composition 340 is used in conjunction with down hole live oil data or down hole live oil samples or down hole dead oil samples to provide a better overall estimate of down hole live oil composition without opening the down hole sampling container.

Figure 4:
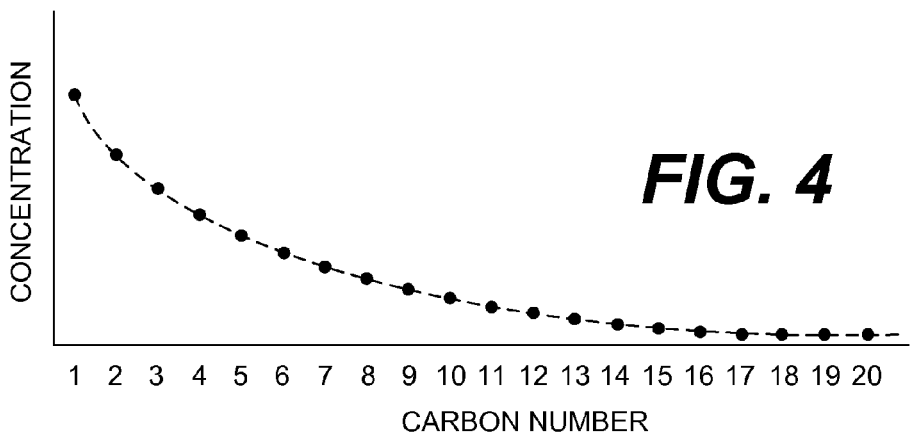
FIG. 4 illustrates a concentration versus carbon number curve for a live oil.
Figure 5:
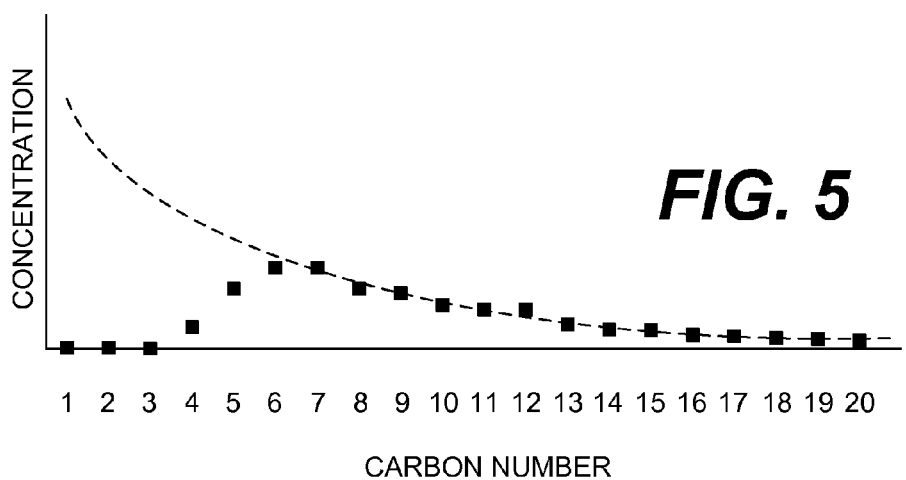
FIG. 5 illustrates a concentration versus carbon number curve for a dead oil, after flashing has occurred.

FIGS. 4 and 5 illustrate the use of constraints 330 to infer the live oil composition 340 from the dead oil composition 315. FIG. 4 shows the composition of a live oil collected in a well. The live oil consists of a number of hydrocarbons, such as saturates, aromatics, resins, asphalts, etc., that can characterized by their carbon numbers (i.e., C1, C2, . . . , etc.). As can be seen, the concentration of different components in the live oil decreases steadily as the carbon number increases. FIG. 5 shows the dead oil composition 315 after flashing has occurred. As can be seen, the dead oil composition 315 shown in FIG. 5 deviates from the live oil composition shown in FIG. 4. Some of the lighter components of the dead oil, e.g. at C1, C2, and C3, have disappeared entirely while others, e.g., at C4, C5, and C6, show smaller but detectable values. Other values show measurement errors or contaminations.

In one embodiment, the dead oil concentration shown in FIG. 5 can be analyzed by finding the peak, or the point at which the concentration numbers stop increasing and begin to decrease. In one embodiment, this point is called the light end loss break point. As can be seen from FIG. 5, this is the point (i.e., approximately at C7) where the dead oil concentration begins to track the live oil concentration, which is indicated in FIG. 5 by the dashed line. The concentration values for higher carbon numbers, constraints, such as those described above, and equations-of-state, such as Henry's Law, can be used to estimate the levels of components lighter than those associated with the light end loss break point.

Henry's Law (at constant temperature) is:

$$p = k_H c$$

where:
  p is the partial pressure of the solute in the gas above the solution;
  c is the concentration of the solute; and
  $k_H$ is a constant that is specific for each solute.

Henry's law defines a relationship between the solubility of different solutes in solutions. The relationship defines a set of ratios that can be used to reconstruct the composition of a solution.

One of the equations of state that is useful in this application is the ideal gas law:

$$PV = \left(\sum_{1}^{N} n_i\right)RT$$

where:
P is pressure (in pascals);
V is volume (in cubic meters);
$n_i$ is the number of moles of the ith component;
R is the ideal gas constant (8.314472 J/(mol–K)); and
T is temperature (degrees Kelvin).

Using this equation it is possible to constrain the state of the system if the composition (i.e., the values of $n_i$) of the live oil is known.

For example, in one embodiment, assume that the dead oil concentrations are as shown in FIG. 5 and other information, e.g., one or more of the constraints discussed above, indicates that formation from which the dead oil was extracted should produce live oil with a concentration-to-carbon-number curve that has the shape of the dashed line in FIG. 5. In one embodiment, once it is recognized that the lighter solutes (i.e., C1-C6 in FIG. 5) have flashed out of solution by identifying the inversion point at C7 as discussed above, a computer program can fit the curve of the shape of the dashed line in FIG. 5 to the points at C7 and heavier. In one embodiment, the resulting curve can be used to estimate the lighter components of the live oil.

Capturing a Micro Live Oil Sample

In one embodiment, the arrangement shown in FIG. 2 is used to take down hole samples. In one embodiment, the flash is performed in a controlled manor to perform a true live oil composition. Alternatively, in one embodiment, a gas capture device is used to sample the gas composition and or gas volume flashed from the connecter without a valve modification to the down hole sampling tool. In one embodiment, as described in U.S. Pat. No. 7,251,565, which is assigned to the assignee of this application, down hole micro samplers obtain live down hole fluids for analysis. In one embodiment, live oil parameters obtained down hole or by sample container QC provide an estimate of the representation of the micro sample to the bulk fluid.

Determining Live Oil Contamination Level

In one embodiment, once the live oil composition is determined, a dead oil contamination level 320 is related to a live oil contamination level 335. This live oil contamination level is more representative of the contamination level in the sample container than that of the dead oil. In one embodiment a surface data logging unit mud filtrate log is used to enhance the dead oil contamination level.

Quality Control

In one embodiment, a dead oil composition provides an inherent traceable QC mark for every fluid. Often surface laboratories can confuse samples, analysis, or alter samples. Because the dead oil composition is representative of the heavier portion of the live fluid captured in the sample chamber, costumers have a composition to check the values of a surface laboratory compositional assay. In one embodiment, because the fluid composition is inherent to the sample fluid and not the sample fluid container the traceable information surpasses all sample transfers and sub sampling. In one embodiment, dead oil "fingerprints" are usually representative for components of volatility less than that of heptanes. In one embodiment, a live oil estimated composition provides QC for a surface laboratories flash. Generally, if flashes are not done properly recombination compositions can differ significantly.

Modeled Physical Properties

In one embodiment, simulated physical properties are the direct output of equation-of-state modeling for live fluid samples obtained in the process described above. Although some of these physical properties are the tiebacks to a live fluid estimation, in one embodiment the process of using multiple tieback properties yields a better set of simulated properties than any single tieback property. Additionally, in one embodiment, the equation-of-state modeling yields physical properties not used for tieback. In one embodiment, these properties are used by costumers in making immediate high dollar decisions concerning the drilling process.

Direct Chemical Property Determination

In one embodiment, the direct chemical compositional determination of an estimated live fluid composition is used to determine chemical properties of the estimated live fluid. These properties can be useful in designing recovery strategies. Often during a true scientific laboratory analysis, not all possible analysis are undertaken in order to save money. A priori knowledge of the composition can more effectively allow customers to select which analyses are most important to perform both in an effort to save money, but also to ensure all essential information is obtained in a timely manner.

Experimental Data

Figure 6:
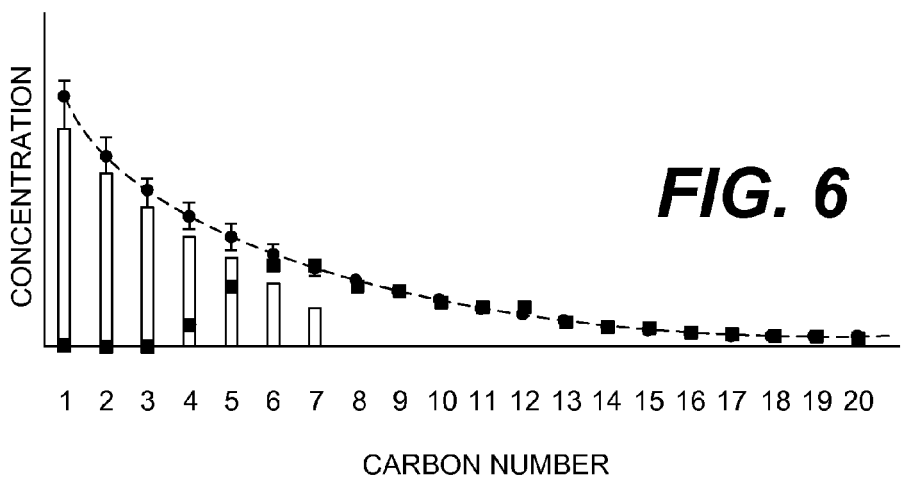
FIG. 6 illustrates a live oil concentration versus carbon number curve inferred from a dead oil sample.

The inventors have conducted an experiment in which dead oils were reconstituted to live oil compositions. As part of this project, the inventors estimated the live oil composition of a dead oil. The inventors used a normal marine trend of composition for a dead oil to predict light end concentrations. In particular, the inventors used a dead oil sample obtained from the North Sea. The biomarker data for the dead oil sample indicated that it was a normal marine oil. The results are shown in FIG. 6. The dead oil showed a break point of C7 as was expected, and the inventors reconstituted components C7 and lighter according to the concentrations of the normal alkane components given by the hollow bars shown in FIG. 6. However, not all of the components more volatile than C7 are normal alkanes. In order to calculate a GOR for the estimated live oil, the inventors extrapolated the distribution non normal alkane components by the same amount using vapor pressure principals, in particular, ratios from C4, C5, and C6. Since vapor pressure is essentially proportional to retention time on a GC-FID, effectively the GC-FID data was used to derive the fractionation values.

The GOR of the sample was then calculated as the standard stock tank volume of components C1 and higher but not including C5, and ½ C5 components ratioed to the remaining components. The normal paraffin weight percents of the oil from a SARA-PIN analysis were used to calculate the effective volume of the whole oil to which the gas components were rationed. The API of the dead oil was measured as 27.7 which is within range for a composition containing 10% asphaltenes. A GOR of 248 SCF/BBL was obtained.

To check the plausibility of the predicted composition, the results were compared to a GOR-API trend for the north sea in J. Wendebourg, and S. J. Duppenbecker, Multidimensional basin modeling, AAPG/Datapages Discovery Series No. 7, p. 137-154. Using information from the paper, the inventors constructed a graph showing the API-GOR trend with error bars as shown in FIG. 7.

Figure 7:
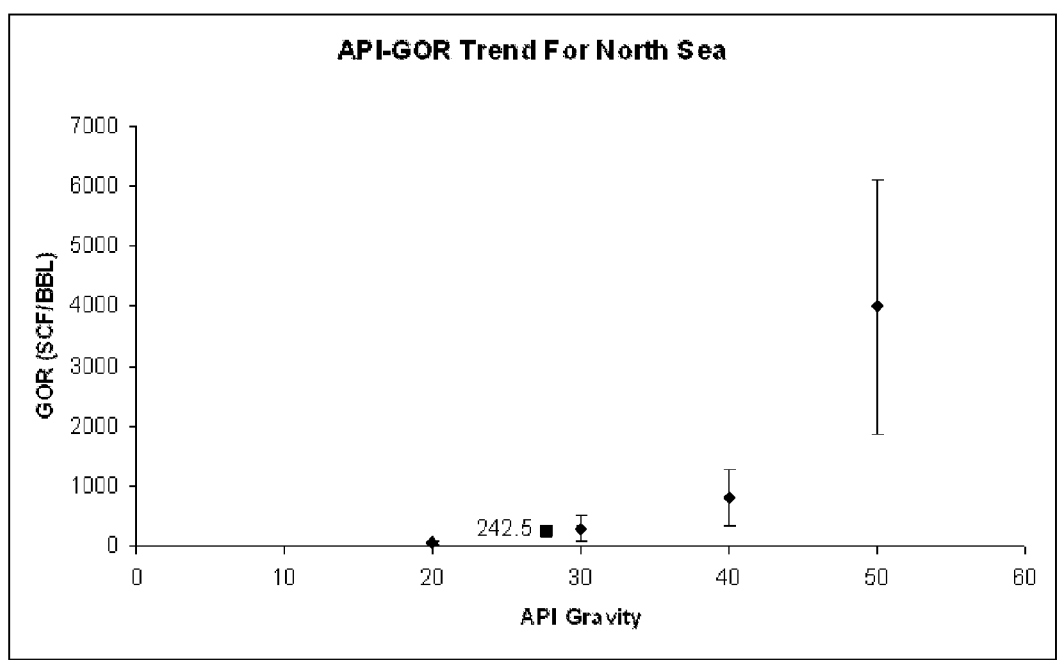
FIG. 7 illustrates a comparison of experimental results to published GOR data.

Although the error bars in FIG. 7 are large, the sample at a GOR of 242.5 tracks the trend in the published data confirming that the predicted GOR is within range. In one embodiment, the reconstitution concentration of components could have been determined by forward modeling the GOR composition based on the calculation until it matched the estimated value of 242.5. It is believed that the reconstituted GOR composition matches the trend well because the sample is of unaltered normal marine composition with "no contamination" because it was obtained at the separator in a flow test from a single zone. More specifically the sample is an ideal sample fitting an ideal curve. This sample was chosen out of about 150 dead oil samples on hand because of the ideal nature of the sample. However even if an ideal sample were not chosen using down hole live oil properties as tiebacks is would have been possible to calculate a live oil estimate.

Figure 8:
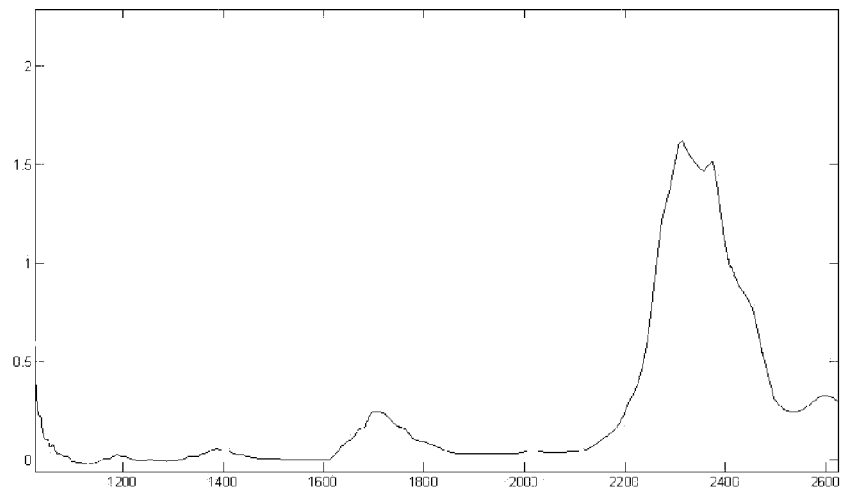
FIG. 8 is a graph of the optical density of a live oil sample measured during an experiment.
Figure 9:
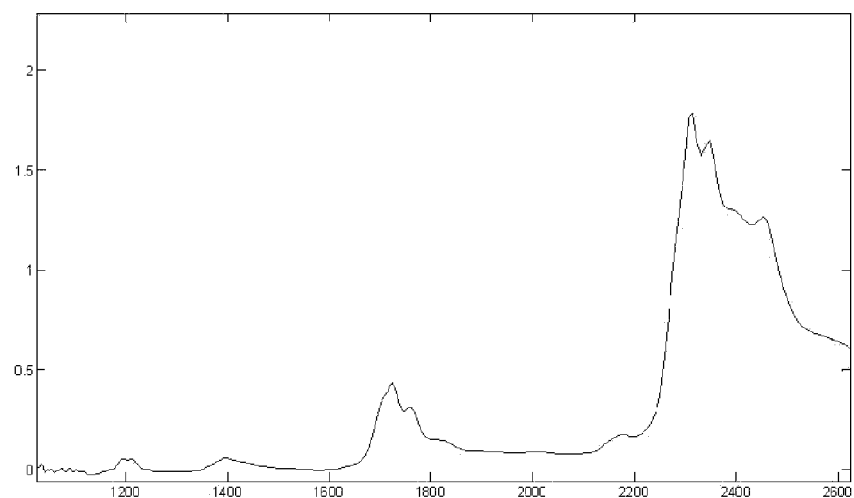
Figure 11:
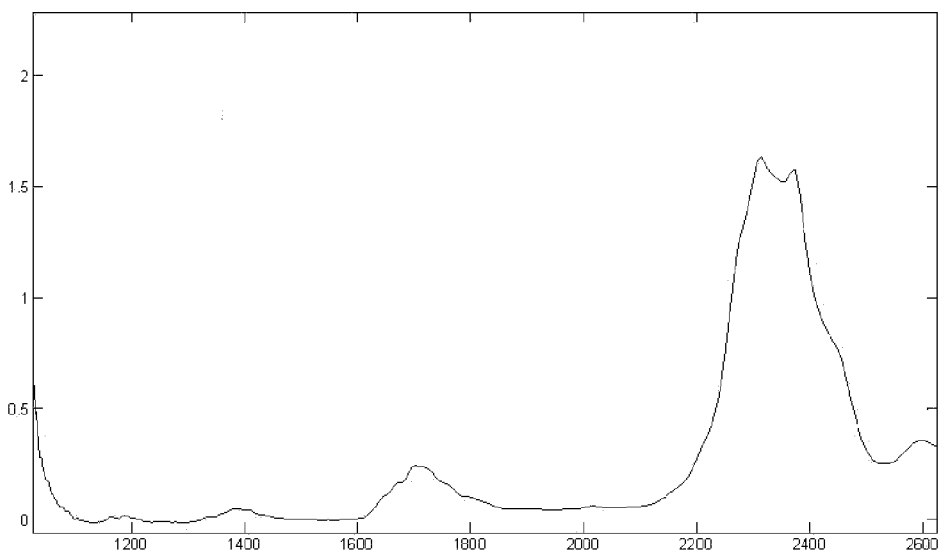
Figure 12:
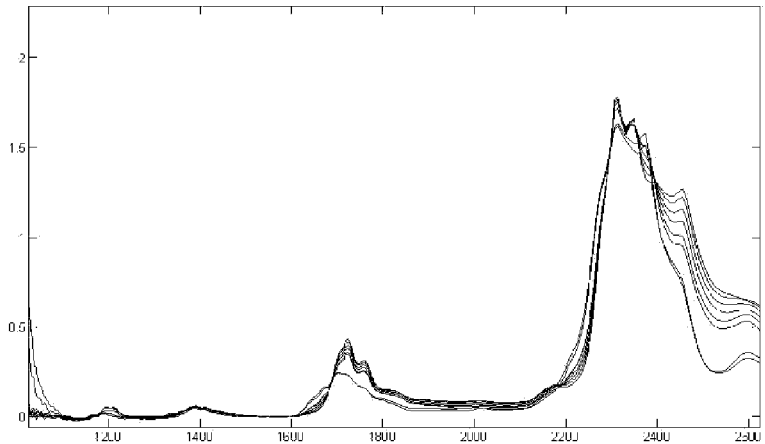

In addition, the inventors ran an experiment using a live oil sample that was retrieved from the well bore. The optical density of the live oil was measured at reservoir temperature and pressure producing the data illustrated in FIG. 8 (in FIG. 8, as in FIGS. 9-12, the horizontal axis is wavelength in nanometers and the vertical axis is optical density, the measured gas concentration is 92 percent, the predicted gas concentration is 94 percent, the RSQ is 0.9899 and the error is 2.6 percent). A portion of the live oil was then flashed to produce a dead oil sample. The optical density of dead oil was measured, producing the data shown in FIG. 9. The composition of the flashed gas was known from a mud gas log taken by a surface data logging unit at the well bore where the live oil sample was taken. Thus, the composition of the gas was known but the amount of gas in the oil was not known. The experiment continued by using the flashed composition as a constraint and recombining the dead oil with the flashed gases, either physically or mathematically, producing the progression of data illustrated in FIG. 10, until the optical density of the recombined dead oil substantially matched that of the live oil, as shown in FIG. 11. FIG. 12 shows FIGS. 8-11 overlaid on each other. In the experiment, the predicted GOR closely matched the measured GOR. Additionally, in a physically recombined system (i.e., where the dead oil is physically recombined with gas), physical pressure, volume, and temperature ("PVT") properties can be measured. Further properties can be extrapolated using equation of state modeling.

Figure 13:
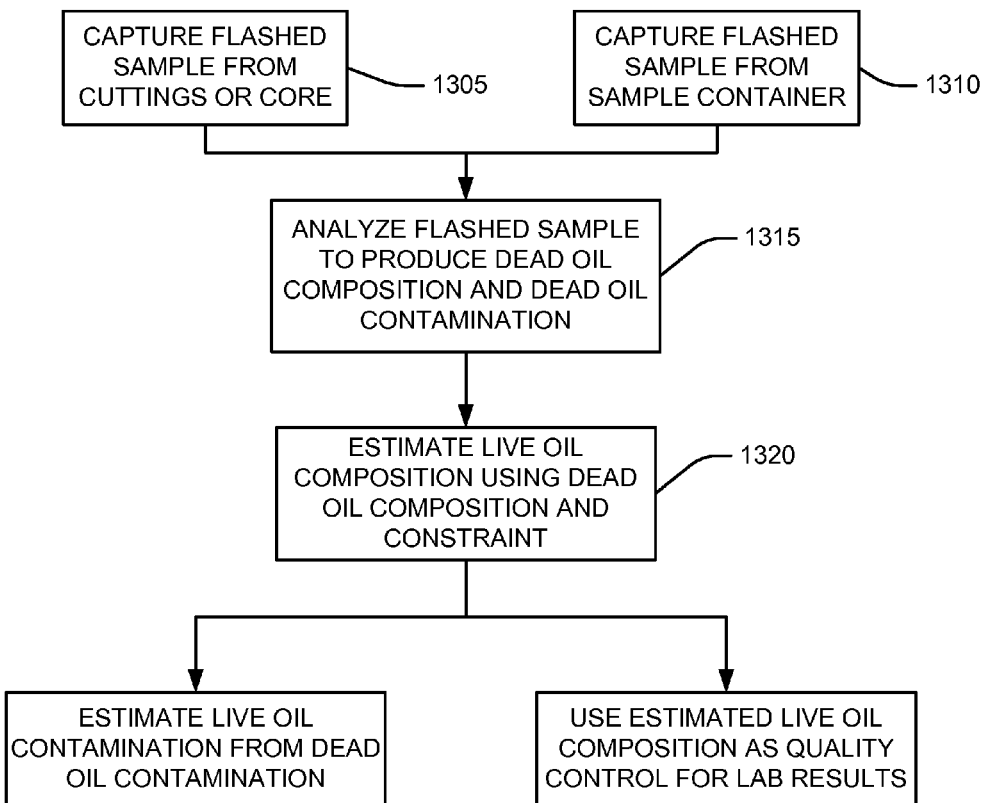
FIG. 13 is a flow chart of a system for estimating live oil concentration and contamination from a dead oil sample.

To summarize one embodiment, as shown in FIG. 13, a flashed sample is captured from cuttings or core samples (block 1305) or from a sample container (block 1310). In one embodiment, the flashed sample is analyzed to produce a dead oil composition and a dead oil contamination (block 1315). In one embodiment, the live oil composition is then estimated using the dead oil composition and one or more constraints (block 1320). In one embodiment, the live oil composition and the dead oil contamination are used to estimate the live oil contamination (block 1325). In one embodiment, the live oil composition is used as a quality control for laboratory results (block 1330).

Figure 14:
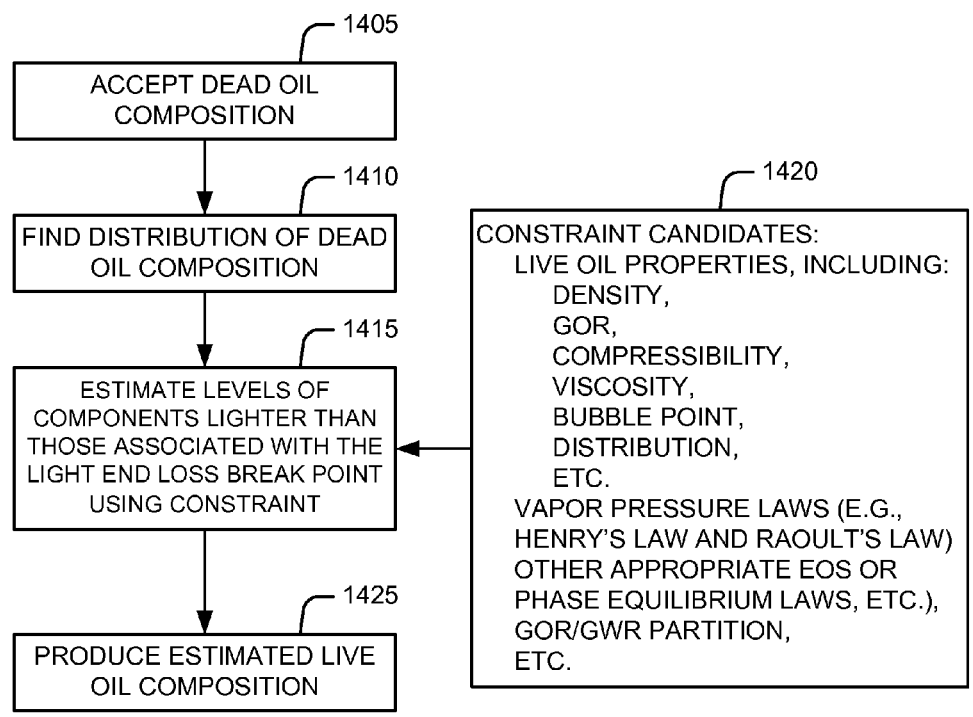
FIG. 14 is a flow chart of one approach to estimating live oil composition from a dead oil composition.

In one embodiment of the process for estimating live oil composition from a dead oil composition, illustrated in FIG. 14, a dead oil composition is accepted (block 1405). In one embodiment, a distribution of dead oil composition, such as that shown in FIG. 5, is then determined (block 1410). In one embodiment, the levels of the components lighter than those associated with the light end break point (e.g., C7 in FIG. 5) are then estimated using one or more constraints (block 1415). In one embodiment, the constraints include, but are not limited to live oil properties (including density, GOR, compressibility, viscosity, bubble point, distribution, etc.), vapor pressure laws (including Henry's Law, Raoult's Law, other EOS or phase equilibrium laws, etc.), GOR/GWR partition, etc. (block 1420). In one embodiment, the estimated live oil composition is then produced (block 1425).

Figure 15:
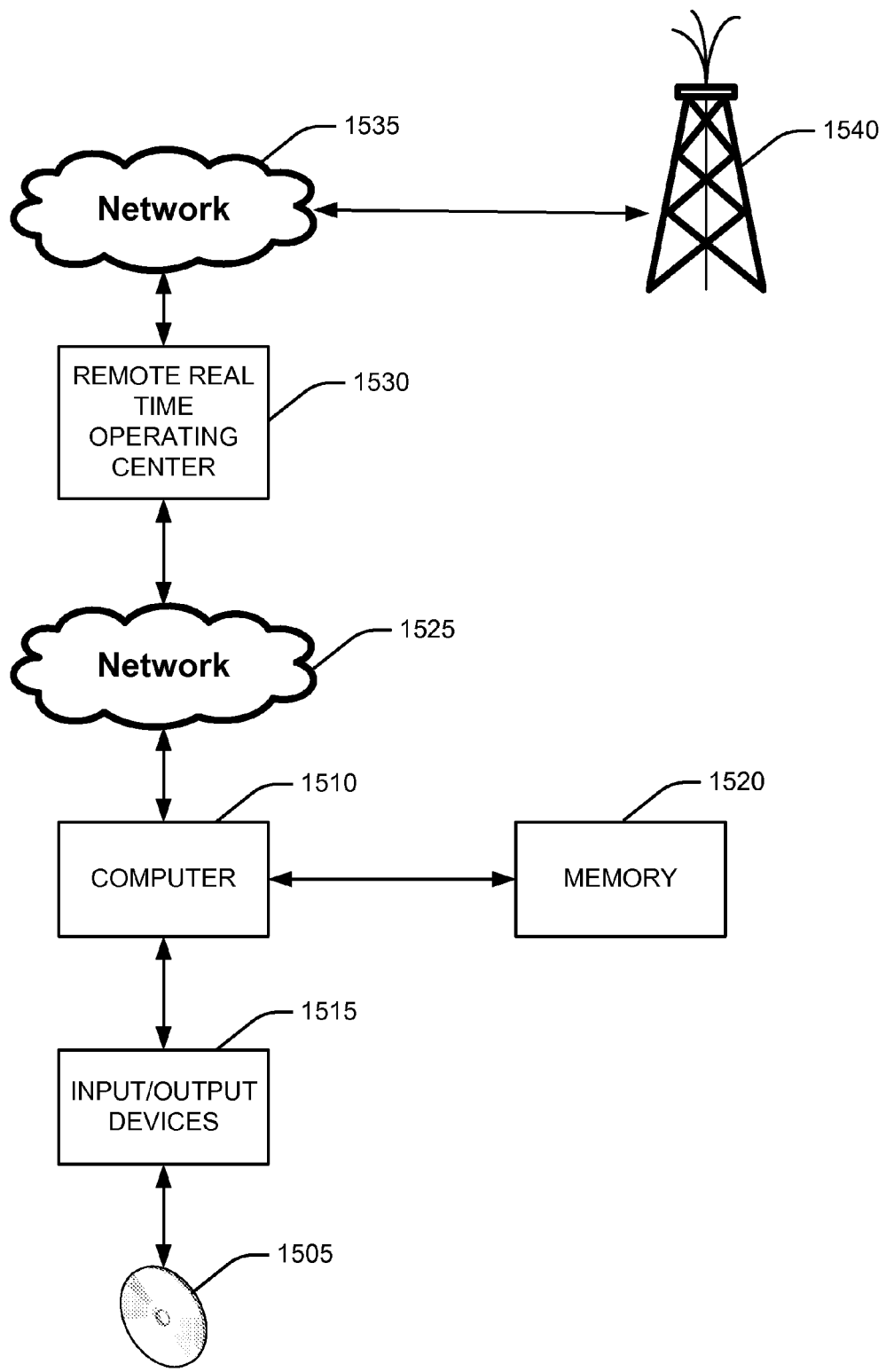
FIG. 15 is an illustration of an environment including a remote real time operating center.

In one embodiment, a computer program for controlling the operation of one of the systems shown in FIG. 1 is stored on a computer readable media 1505, such as a CD or DVD, as shown in FIG. 15. In one embodiment a computer 1510, which may be the computer 140, a computer in the analysis system 165, or a computer located below the earth's surface, reads the computer program from the computer readable media 1505 through an input/output device 1515 and stores it in a memory 1520 where it is prepared for execution through compiling and linking, if necessary, and then executed. In one embodiment, the system accepts inputs through an input/output device 1515, such as a keyboard, and provides outputs through an input/output device 1515, such as a monitor or printer. In one embodiment, the system stores the results of calculations in memory 1520 or modifies such calculations that already exist in memory 1520.

In one embodiment, the results of calculations that reside in memory 1520 are made available through a network 1525 to a remote real time operating center 1530. In one embodiment, the remote real time operating center 1530 makes the results of calculations available through a network 1535 to help in the planning of oil wells 1540, in the drilling of oil wells 1540, or in production of oil from oil wells 1540. Similarly, in one embodiment, the systems shown in FIG. 1, 2, or 3 can be controlled from the remote real time operating center 1530.

The text above describes one or more specific embodiments of a broader invention. The invention also is carried out in a variety of alternate embodiments and thus is not limited to those described here. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A system for estimating a live-oil hydrocarbon composition of a reservoir fluid sampled from a well drilled by a drill string, the system comprising:
   a formation testing tool having a manifold for carrying sampled reservoir fluid to a plurality of sample chambers and a removable tube for carrying sampled reservoir fluid from the manifold to a sample chamber, the tube to contain a sample of the reservoir fluid from the well, the tube being closeable so that the tube can be removed from between the manifold and the sample chamber while retaining the contents of the tube;
   an analysis processor to receive the sample from the tube after the tube has been removed from the formation testing tool and after volatile hydrocarbon components of the sampled reservoir fluid within the tube have substantially vaporized and to measure a hydrocarbon composition of the sample;
   an inference processor to accept the measured hydrocarbon composition and a constraint;
   wherein the inference processor is configured to analyze the measured hydrocarbon composition of the reservoir fluid by solving a system of N simultaneous equations of state, N>1, having a plurality, greater than N, of unknowns and the constraint useful to eliminate some of the plurality of unknowns to produce an estimated live oil hydrocarbon composition of the reservoir fluid before the volatile hydrocarbon components have substantially vaporized.

2. The system of claim 1 wherein the constraint is a live oil property selected from a group of live oil properties consisting of live oil density, live oil gas-to-oil ratio, live oil compressibility, and live oil viscosity.

3. The system of claim 1 wherein the constraint is a known pattern of components.

4. The system of claim 1 wherein the constraint is defined by the reservoir.

5. The system of claim 1 wherein when analyzing the measured hydrocarbon composition of the reservoir fluid and a constraint, the inference processor:
   estimates the levels of the components lighter than those associated with a light end loss break point using the constraint.

6. The system of claim 1 further comprising:
   a first valve coupled to the tube for connecting the tube to the manifold;
   a second valve coupled to the tube for connecting the tube to the sample chamber; and
   the first valve and the second valve being closeable so that the tube can be removed from between the manifold and the sample chamber while retaining the contents of the tube.

7. A method for estimating a live-oil hydrocarbon composition of a reservoir fluid sampled from a well drilled by a drill string, the method comprising:
   collecting a sample of reservoir fluid from a well using a formation testing tool having a manifold for carrying sampled reservoir fluid to a plurality of sample chambers and a removable tube for carrying sampled reservoir fluid from the manifold to a sample chamber, the tube to contain the sample of the reservoir fluid from the well, the tube being closeable so that the tube can be removed from between the manifold and the sample chamber while retaining the contents of the tube;
   using an analysis processor to measure the hydrocarbon composition of the sample from the tube after the tube has been removed from the formation testing tool and after volatile hydrocarbon components of the sampled reservoir fluid within the tube have substantially vaporized;
   using an inference processor to analyze the measured hydrocarbon composition of the reservoir fluid to produce an estimated live-oil hydrocarbon composition of the reservoir fluid before the volatile hydrocarbon components have substantially vaporized.

8. The method of claim 7 wherein a constraint used by the inference processor is a live oil property selected from a group of live oil properties consisting of live oil density, live oil gas-to-oil ratio, live oil compressibility, and live oil viscosity.

9. The method of claim 7 wherein a constraint used by the inference processor is a known pattern of components.

10. The method of claim 7 wherein a constraint used by the inference processor is defined by the reservoir.

11. The method of claim 7 wherein analyzing the measured hydrocarbon composition of the reservoir fluid and a constraint comprises:
    estimating the levels of the components lighter than those associated with a light end loss break point using the constraint.

* * * * *